(12) United States Patent
Haveri

(10) Patent No.: US 8,166,798 B2
(45) Date of Patent: May 1, 2012

(54) GAS ANALYZER HAVING A STRUCTURE INCLUDING CAVITIES AND VOLUMES

(75) Inventor: Heikki Haveri, Huhmari (FI)

(73) Assignee: General Electric Company, Schenectady, NY (US)

( * ) Notice: Subject to any disclaimer, the term of this patent is extended or adjusted under 35 U.S.C. 154(b) by 783 days.

(21) Appl. No.: 12/164,863

(22) Filed: Jun. 30, 2008

(65) Prior Publication Data

US 2009/0320558 A1 Dec. 31, 2009

(51) Int. Cl.
*G01N 1/22* (2006.01)
*G01N 33/497* (2006.01)

(52) U.S. Cl. .......................................... 73/23.3

(58) Field of Classification Search ............... 73/23.3, 73/23.42; 156/256; 366/340
See application file for complete search history.

(56) References Cited

U.S. PATENT DOCUMENTS

| | | | | |
|---|---|---|---|---|
| 5,000,052 | A * | 3/1991 | Sipin | 73/863.03 |
| 5,069,063 | A * | 12/1991 | Chrobaczek et al. | 73/114.26 |
| 5,537,860 | A * | 7/1996 | Haertl | 73/54.14 |
| 6,701,774 | B2 * | 3/2004 | Srinivasan et al. | 73/23.42 |
| 6,772,513 | B1 | 8/2004 | Frye-Mason | |
| 7,132,650 | B1 * | 11/2006 | Gamble et al. | 250/288 |
| 7,730,766 | B2 * | 6/2010 | Ryser et al. | 73/30.04 |
| 2004/0043479 | A1 | 3/2004 | Briscoe | |
| 2008/0163674 | A1 * | 7/2008 | Bonne et al. | 73/31.05 |
| 2009/0207568 | A1 | 8/2009 | Haveri | |

FOREIGN PATENT DOCUMENTS

EP 1707940 11/2009

OTHER PUBLICATIONS

Schmid U; Seidel H; Mueller G; Becker TH: "Theoretical considerations on the design of a miniaturised paramagnetic oxygen sensor", Sensors and Actuators B, Jul. 28, 2006, pp. 213-220, vol. 116, No. 1-2, Elsevier Sequoia S.A., Lausanne, CH.

Gangora-Rubio M; Sola-Laguna LM; Moffett P J; Santiago-Aviles J J: "The utilization of low temperature co-fired ceramics (LTCC-ML) technology for meso-scale EMS, a simple thermistor based flow sensor", Sensors and Actuators A, Mar. 30, 1999, pp. 215-221, vol. 73, No. 3, Elsevier Sequoia S.A., Lausanne, CH.

Ibanez-Garcia; Alonso N; Martinez Cisneros J; Valdes C S; F: "Green-tape ceramics. New technological approach for integrating electronics and fluidics in microsystems", Trac, Trends in Analytical Chemistry, Dec. 26, 2007, pp. 24-33, vol. 27, No. 1, Elsevier, Amsterdam, NL.

Gongora-Rubio M R et al: "Overview of low temperature co-fired ceramics tape technology for meso-system technology (MsST)", Sensors and Actuators A, Apr. 15, 2001, pp. 222-241, vol. 89, No. 3, Elsevier Sequoia S.A., Lausanne, CH.

Pietrikova A: "Potentiality of LTCC for sensor applications", Electronics Technology: Concurrent Engineering in Electronic Packaging 2001. 24th International Spring Seminar on May 5-9, 2001, pp. 112-116, Piscataway, NJ, USA, IEEE.

* cited by examiner

*Primary Examiner* — John Fitzgerald

(74) *Attorney, Agent, or Firm* — Andrus, Sceales, Starke & Sawall, LLP

(57) ABSTRACT

Method of making a structure, a structure and a gas analyzer comprising cavities and volumes in which a multilayer structure is made by laminating single layers on top of each other to form the multilayer structure and combining them all together, in which method before the laminating step at least one layer is processed by cutting pneumatically constrictive openings therein to form pneumatic filters comprising constrictive cavities and volumes with the surfaces of the adjoining layers.

8 Claims, 3 Drawing Sheets

GAS ANALYZER HAVING A STRUCTURE INCLUDING CAVITIES AND VOLUMES

BACKGROUND OF THE INVENTION

The disclosure relates generally to a low temperature cofired ceramic structure and a method of making such structure.

Precision pneumatic suppressors are commonly used in for example medical devices and systems to generate accurate pressure drop over the predetermined precision suppressor. The pressure drop generated by the suppressor may be used for protecting a pressure sensitive device such as pressure sensor. Furthermore the magnitude of the pressure drop can be measured with a differential pressure measurement connected over the suppressor and that pressure information can be further used to determine the fluid flow rate through the channel. Moreover precision suppressors can be used to adjust accurate fluid flow rates and flow ratios between two or more channels that form a net of channels, which connect together at one point. Fluid flow rate though each channel is adjusted by the absolute constriction of that specific channel together with the constriction ratio of precision suppressors in respect to constrictions in other channels. Another form of application is to connect suppressors to volumes to form pneumatic filters to filter alternating pressures and noise in the system etc. The frequency band of such filter can be adjusted with the magnitude of suppression and the size of the volume.

Conventional precision stainless steel tubes are commonly used to generate accurate pneumatic constrictions. Manufacturing tolerances of such precision stainless steel tubes are rather high and the constriction they produce may deviate more than 25% from its nominal value. Some devices are extremely sensitive for such tolerances. Of course by measuring the value of constriction of each suppressor, then sorting and selecting pieces that are within the manufacturing specification, can increase the manufacturing yield of produced devices. On the contrary this kind of manufacturing process is time consuming, uneconomical and first of all very expensive. Precision stainless steel tubes are usually connected to tubing or similar by hand. They can also be placed inside a plastic mould including some larger cavities as well as input and output ports outside the mould to connect suppressors to a device or a system. As suppressors need to be connected to tubing or a plastic mould the device size is increased considerably making it clumsy. Each connection between the tubing and, or plastic mould also causes a risk of leakage.

Low Temperature Co-fired Ceramics (LTCC) is a well-established process that has been in use for many years in the microelectronics packaging industry. It is similar to the thick film hybrid process employed for multilayer ceramic capacitors and chip inductors. LTCC technology is especially used for wireless and high-frequency applications. In RF and wireless applications, LTCC technology is also used to make multiplayer hybrid integrated circuits, which can include resistors, inductors, capacitors, and active components in the same package. In general LTCC hybrids have a smaller initial cost as compared with for example ICs, making them an attractive alternative for small-scale integration devices. It is also known to use said LTCC process to make elements having micro-channels and cavities for fluids. These known solutions are however only designed for through flow of a medium, i.e. having no intention to create pneumatic constrictions.

BRIEF DESCRIPTION OF THE INVENTION

The above-mentioned shortcomings, disadvantages and problems are addressed herein which will be understood by reading and understanding the following specification.

In an embodiment a method of making a structure comprising cavities and volumes in which method a multilayer structure is made by laminating single layers on top of each other to form the multilayer structure. The layers are all combined together. Before the laminating step at least one layer is processed by cutting pneumatically constrictive openings therein to form pneumatic filters comprising constrictive cavities and volumes with the surfaces of the adjoining layers.

In another embodiment a structure compresses cavities and volumes. The structure is a multilayer structure obtained by laminating single layers on top of each other to form the multilayer structure and combining them all together. The cavities and volumes are made before the laminating step by cutting pneumatically constrictive openings at least to one layer to form pneumatically constrictive openings therein to form pneumatic filters. The pneumatic filters comprise constrictive cavities and volumes with the surfaces of the adjoining layers. At least one of the outer surfaces of structure are provided with connections for surface mounted devices.

In yet another embodiment gas analyser comprises a structure comprising cavities and volumes. The structure is a multilayer structure obtained by laminating single layers on top of each other to form the multilayer structure and combining them all together. The cavities and volumes are made before the laminating step by cutting pneumatically constrictive openings at least to one layer to form pneumatic filters comprising constrictive cavities and volumes with the surfaces of the adjoining layers. At least one of the outer surfaces of structure is provided with connections for surface mounted devices. The surface mounted devices comprise pneumatic inlets/outlets and pneumatic or/and electronic components.

Various other features, objects and advantages of the disclosure will be made apparent to those skilled in the art from the accompanying drawings and detailed description thereof.

DETAILED DESCRIPTION OF THE INVENTION

The invention will now be described in greater detail by means of preferred embodiments of the invention illustrated in the attached drawing LTCC can be defined as a multilayer circuit fabricated by laminating single greensheets, term for unfired tapes used to form one layer of the multiplayer board, with printed low resistivity conductor lines etc. on the surface on top of each other and firing them all together in one step. It is also possible to integrate passive elements like resistors, capacitors and inductors into the substrate, which reduces circuit dimensions. The technology is primarily designed for manufacturing highly developed electronic circuits, but it can be applied to manufacture reproducible, low tolerance, precision cavities of various shapes and sizes in a fully automated process. These cavities can be used to generate various pneumatic lines for example for fluids and cavities can be further connected to sensing devices such as pressure sensors integrated into LTCC that contains electrical circuitry as well. The technology is inexpensive compared to conventional techniques since multilayer circuits are fabricated as a batch of several circuit boards in one panel in fully automated manufacturing process. Additional components, etc. are also placed and the whole system tested in an automated process. As a last step of fabrication circuits are cut apart as finished multilayer circuit boards. Size of the panel is usually several inches or more, thus one panel may contain up to hundreds of boards depending on the board and the panel size. The manufacturing process is very stable as physical properties and mechanical behaviour of materials used during fabrication is well known thus making the final product very accurate.

Figure 1:
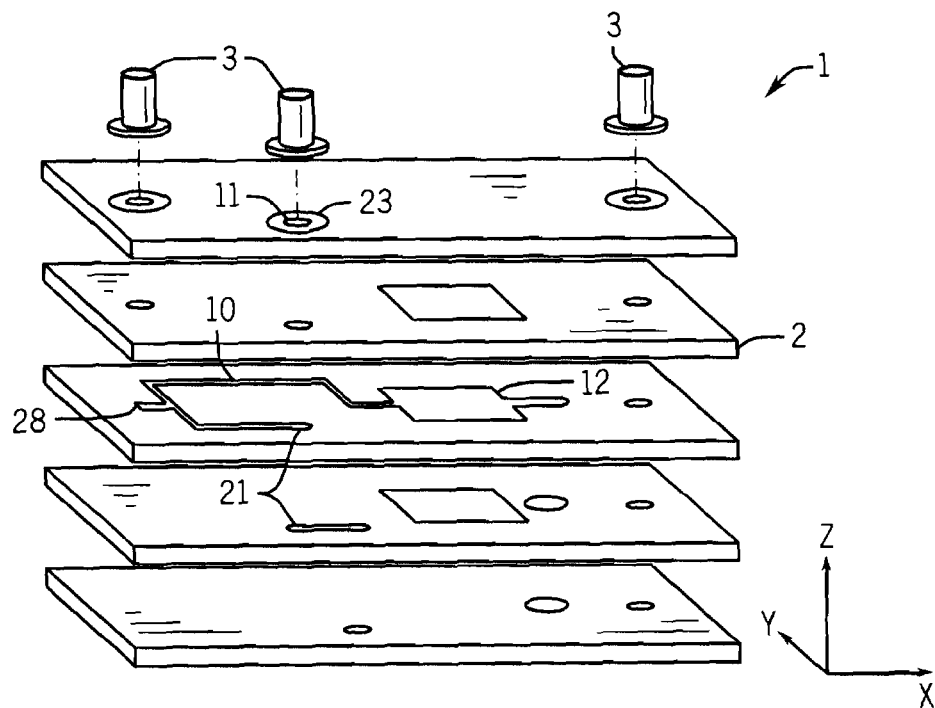
FIG. 1 shows an exploded view of one embodiment of an example multilayer circuit provided with pneumatically constrictive channels.
Figure 2:
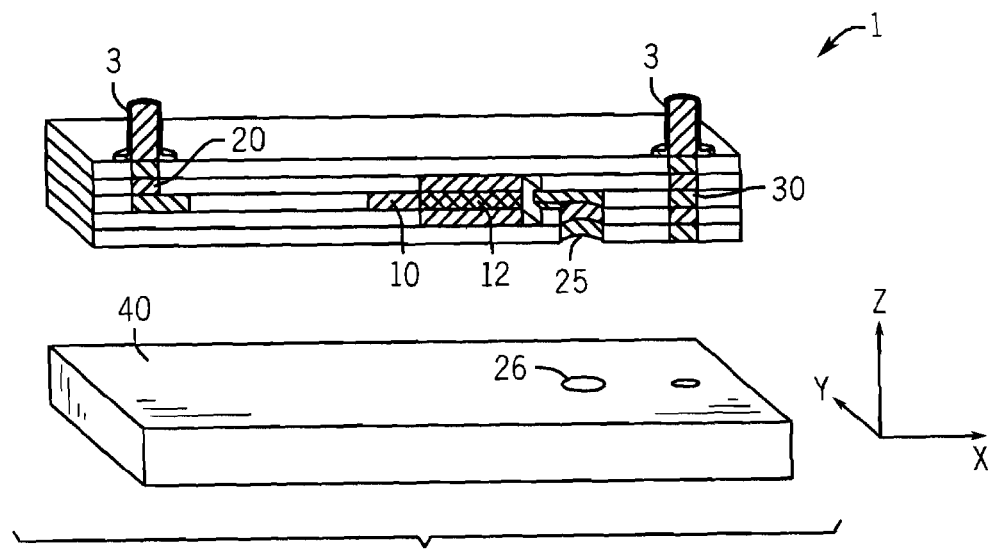
FIG. 2 shows a cross sectional view of the circuit along the cross sectional line shown in FIG. 1, and FIGS. 3, 4 and 5 show different alternative constructional details in XY-direction of FIGS. 1 and 2 to obtain pneumatic constrictions.

FIG. 1 shows an exploded view of an example multilayer LTCC circuit 1 in which the layers are formed by greensheets. FIG. 1 shows the structure in the situation before greensheets are laminated, fired and before Surface Mounted Devices (SMD) are mounted on the board. FIG. 2 shows a cross sectional view of that same LTCC circuit after it is processed along the cross sectional line shown in FIG. 1. The example multilayer LTCC circuit 1 shown in FIGS. 1 and 2 is constructed of five layers made by greensheets 2. Surface mounted devices such as inlets and outlets 3 have been placed on the top surface of LTCC, but SMD can consist of electronic components or similar as well, which are not shown in FIGS. 1 and 2.

Greensheets 2 are manufactured in several standard thicknesses and the thickness of a single greensheet is approximately between 50 µm and 400 µm. The maximum number of greensheets, that can be used to implement a multilayer LTCC circuit 1, depends on the size of the substrates plane area and the thickness of greensheets used. Smaller plane area and higher layer thickness decrease the number of layers that can be used since the lamination becomes more difficult as the multilayer circuit tends to collapse during the manufacturing process. In a favourable case multilayer LTCC pneumatic circuit including cavities and electronics circuitry in several different layers can be implemented of even 40 layers or more. The maximum height of such multilayer circuit may be several millimeters.

Cavities 10 or volumes 12 are processed in to different greensheets by cutting openings with laser, puncher or similar in to the direction perpendicularly against the greensheets XY-plane. After greensheets are laminated, cavities are formed between the greensheets plane surfaces, one greensheet above and one below the formed cavity. The cross-sectional shape of cavities 10 or volumes 12 is thus approximately a rectangle in the direction of cavity in XZ- or YZ-plane.

Figure 3:
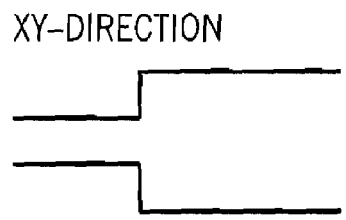
Figure 4:
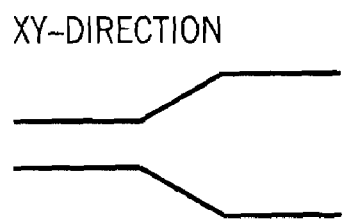
Figure 5:
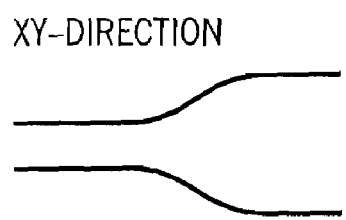

The cross-sectional area and the length of the cavity determine the pneumatic constriction of the cavity. The width of the cavity or volume in XY-plane can vary approximately from tens of micrometers to several millimeters, i.e. the cavities and volumes can be made by dimensioning the whole opening made to a greensheet to form a channel or cavity with a throttling effect or alternatively a widening channel or a volume. The width of the cavity can be altered freely, thus also stop like increments (or decrements) as shown in FIGS. 3, conical as in 4 and specially shaped with continuously changing width as in 5, or any in the flowing direction short narrow points or areas creating a throttling effect, are possible. The minimum width of the cavity is limited by the minimum cutting width of tooling, but it is also limited by fabrication process itself. In lamination cavities in different greensheets may be filled up with material that hold up the cavities and prevent them to collapse. Filling material is then burned off during firing, but if the cavity in too small the burning may be incomplete or the burned material exits from the cavity incompletely. Incompletely burned filling material or the recrement left in the cavity alters the quality of cavities or may even clog the cavities, thus limiting the minimum width as well as the minimum height of the cavity that can be fabricated.

The height of the cavity or volume, in to the direction of Z-axes in FIGS. 1 and 2, is defined by the thickness of greensheets as well as the number of greensheets used to form the cavity. The minimum height of the cavity is thus the minimum thickness of a single available greensheet. The maximum height of the cavity may be several millimeters. The height of the cavity alters in step like increments (or decrements), as shown in FIG. 3, since it is difficult to cut opening, which walls are in an angle in respect of greensheets plane. The height of the stop is determined by the thickness and the number of greensheets used.

The length of the cavity can vary from few micrometers to hundreds of millimeters, but the fabrication process, limits the maximum length of the cavity again. Incompletely burned filling material or the recrement is one cause of limitation, but other relates to the design and lamination. If the designed cavity is complicated lamination becomes more difficult as the two halves, that the cavity divides, can move in regard to each other. This may decrease the accuracy in manufacturing and becomes more dominating as the channel length of the channel is increased. The same applies for the cavity that makes almost 360 degree turn leaving a leaf like area of greensheet.

Cavities and volumes can have different shapes and forms in XY-plane and they can be multi-directional as each cavity can divide in to several different cavities, as shown at point 28 in FIG. 1, or they can join into one cavity common for all. Cavities can turn any circular or sharp angle in the direction of plane and right angle when the cavity shifts to other plane. Each turn affects to the overall constriction of the cavity depending on the "sharpness" of the turn also. Different cavities in adjacent layers can be connected to each other by placing them to overlap as shown by connection 21 in FIG. 1. Cavities that are in different, but not in adjacent layers, can be connected through via.

Via 11, which are perforations entering through one or more layers, are also processed in to different greensheets by cutting them with laser, with a puncher or by drilling in to the direction perpendicularly against the greensheets XY-plane. The cross sectional shape of via, in to the direction perpendicular to LTCC plane, are normally made circular, but they can have any other shape as well. Via can be used to connect cavities to each other that are in different, but not adjacent layers, but similarly via can be used to connect cavities outside LTCC through the plane surfaces as shown by connection 20 in FIG. 2. It is also possible to connect cavities outside LTCC through the edges as well (not shown in FIGS. 1 and 2), but it is more difficult to arrange outlet for the connection. It is also possible to process tubular or any other shape of cavities 30 through via perforating one, several or all the layers in to the direction perpendicular against the greensheets XY-plane.

Connections outside LTCC can further include inlets and outlets 3 mounted on the plane surfaces on the top of via by gluing or soldering them in to the metallization 23 on the surface around via. Cavities can then be coupled in to other systems through tubing or similar connected to inlets and outlets. Other way of connect LTCC in to other systems is to connect via on the plane surface of LTCC, as shown by connection 25, straight to a similar perforations 26 on the plane surface of, for example plastic mould 40 shown in FIG. 2 by gluing or similarly attaching the two adjacent surfaces together so that the opposite perforations confront forming a continuous channel.

The simplest form of precision pneumatic suppressors implemented on LTCC can be straight or curved cavities with inlet and outlet holes or ports on the surface of LTCC. In more sophisticated system precision suppressor can be formed by just a narrowing in the cavity and each cavity can be connected to a net of similar cavities with multiple inputs and outputs. The net of cavities can be used to divide flows, but system can also contain volumes for filtering alternating pressures. Furthermore the system can contain connections to pressure sensors and other similar components with the supporting electronics, such as highly integrated electronic circuitry with SMD components such as paste resistors, buried capacitors and processors to measure and analyse the pneumatic system. System can further contain even valves to control the system composing all-inclusive functioning device within one LTCC board.

Figure 6:
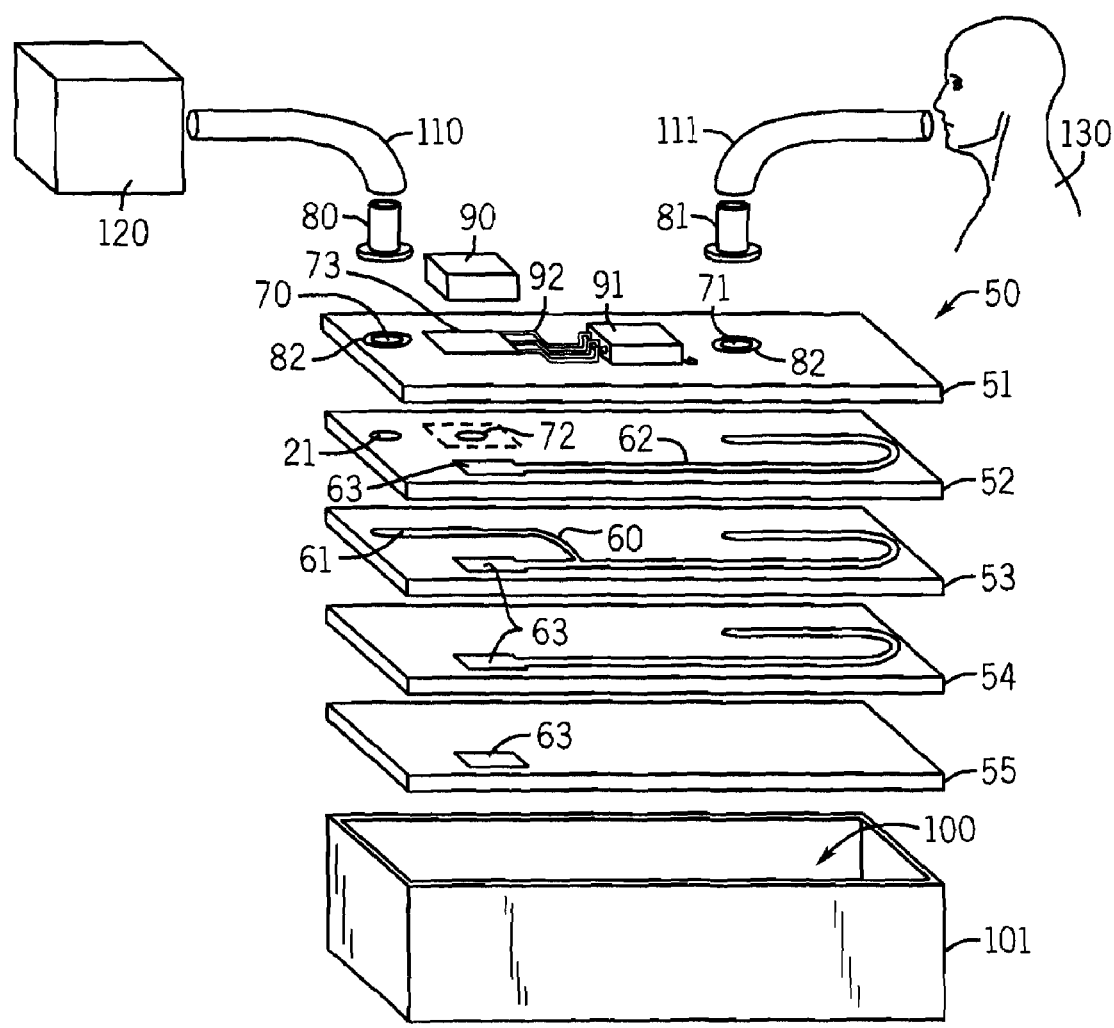
FIG. 6 shows a simplified, exploded and schematic view of a part of a gas analyser.

FIG. 6 shows a simplified, exploded, schematic view of the ceramic board that is used as a part of a gas analyzer that measures the content of oxygen in the breathing gas.

The ceramic board 50 is constructed of five separate layers, layer 51 as a top layer, layers 52, 53 and 54 as inner layers and layer 55 as a bottom layer. All layers contain openings that, as laminated together, form cavities such as a constrictive cavity 60, volumes or pneumatically connective cavities 61 and 62, volume or opening 63 that opens to the bottom side of the board 50, perforations 70, 71 as well as perforation 72 on the bottom of opening 73, which all open to the top side of the board 50. Metallic inlets 80 and 81 can be mounted on perforations 70 and 71 on the top surface of the ceramic board 50 soldering them in to the metallizations 82 around the perforations 70 and 71 to form a continuous cavity in to the pneumatic system inside the ceramic board 60. A pressure sensor 90 can be mounted into the opening 73 in layer 51 by gluing or similarly attaching the bottom surface of the pressure sensor to the top surface of the layer 52 on the bottom of opening 73. Perforation 72 on the bottom of opening 73 then pneumatically connects the pressure sensor into the junction of constrictive cavity 60 and connective cavity 61. The electrical connections (not shown) of the pressure sensor 90 connect to the surface mounted electronics circuitry 91 mounted on the top surface of the ceramic board 50 through electric wires 92 on the top or bottom surfaces or between the inner layers of the ceramic board. The electronics circuitry 91 is used to amplify and electrically filter the signals as well as to convert the signals into the digital form etc. for further processing to get preferably a binary value proportional to the oxygen content in the breathing gas mixture sampled from the patient. Opening 63 on the bottom surface of the ceramic board 50, which is also in connection with the connective cavity 62, opens into a larger space or volume 100 defined by the plastic housing 101 attached on the bottom side of the ceramic board 50. Tubing 110 connects the other end of the pneumatic system inside the ceramic board 50 to the rest of the gas analyzer 120, containing an electromagnet and a gas pump, through the inlet 80 whereas the tubing 111 connects the other end of the pneumatic system to the patient 130.

The gas pump is used to suck the gas sample from the patient through the tubing 111, the pneumatic system inside the ceramic board 50 and through the electromagnet inside the gas analyzer 120. The oxygen is a paramagnetic gas that reacts to the afternating magnetic field by generating an alternating pressure signal, which frequency is proportional to the frequency of alternating magnetic field and the amplitude is proportional to the oxygen content in the gas sample. The optimum frequency for the alternating magnetic field, in terms of efficiency, is between 50-300 Hz, but other frequencies can be used as well. The frequency of alternating pressure signal is between these frequencies also as it travels through the tubing 110 in to the pneumatic system inside the ceramic board 50 and to the pressure sensor 90 that transforms the alternating pressure signal into an electrical signal. The amplitude of the signal is very small thus it has to be amplified and filtered with the electronics circuitry 91.

Usually the patient is connected to a ventilator, which pushes the air into the patient's lungs during inspiration with a pressure higher than atmospheric pressure whereas the air inside the lungs is released to flow out during expiration and the pressure lowers down to atmospheric pressure again. The respiration rates are normally between 10-100 breaths/minute thus the pressure at the patient end of the tubing 111 alternates with a same phase. This alternating pressure travels into the gas analyzer and the pneumatic system inside the ceramic board 50 through the tubing 111 used for taking a gas sample from the patient. There are also other pressure waves such as sounds of talking and sounds from different equipment that also enter the pneumatic system and the pressure sensor as well. The pressure sensor is also disturbed by the hissing noise of high velocity gas traveling through the tubing 111. The amplitude of interfering alternating pressures coming through the tubing are usually much higher than the amplitude of alternating pressure caused by oxygen. The pressure sensor is very sensitive, as it has been adjusted for detecting the small amplitude signal of oxygen, whereas the high amplitude interfering pressures containing multiple frequencies destroy the measured signal or even drive the pressure sensor out from its sensing range. To prevent this gas analyzer pneumatic system contains the connective cavity 62 of suitable length and cross sectional area that is used to slow down and to make laminar the high velocity turbulent flow of sample gas and to pneumatically filter interfering alternating pressures with a pneumatic filter formed by the constrictive cavity 60 that conducts through the connective cavity 62 and opening 63 in to the large volume 100 forming a pneumatic filter. Pneumatic filtering means that undesired frequencies of alternating pressure are eliminated around the frequency of alternating pressure where the gas measurement, for example oxygen measurement, occurs.

FIG. 6 shows a simplified view of the gas analyzer and some parts of the complete system are not shown. In reality the gas pump generates an alternating pressure that also interferes the functioning of the pressure sensor, which is pneumatically filtered with another pneumatic system inside the ceramic board not shown in FIG. 6. Also the gas flow that gas pump generates must be divided between different gas analyzers, which is implemented with parallel and/or serial constrictive cavities inside the ceramic board not shown in FIG. 6.

The advantage of structure and the method described above is in that very accurate and reproducible pneumatic constrictors with very low manufacturing tolerances can be implemented in a multilayer Low Temperature Co-fired Ceramics (LTCC). These precision pneumatic constrictions can be combined to a net of connecting cavities including volumes, connectors as well as supporting devices, such as pressure sensors and electronics, in a same device. The present method, structure and gas analyser is particularly advantageous in connection with precision pneumatic suppressors. Constructing the whole pneumatic system on LTCC reduces conventional connections between tubing, constrictions, volumes etc. simplifying conventional systems and making the overall size smaller. The risk of leakage is also decreased, which improves the functioning of whole system and improves the patient safety in medical applications. Important improvement is the reproducibility, controllability and high accuracy of mechanical measurements to generate extremely accurate suppressors or constrictions, cavities or other similar formations, which are building blocks of a more complex system. Variations between different manufacturing batches are small and the overall accuracy of constriction implemented in LTCC is several times better compared to the best available precision stainless steel constrictions, whereas the cost is smaller at the same time. Different size of constrictions as well as different supporting elements used for composing the system can be easily and cost effectively mass-produced. Difficult, time consuming and error sensitive handwork is decreased, which in turn decreases the expense of the system even more.

The embodiments described above are by no means intended to restrict the disclosure but the embodiments may be modified completely freely within the scope of the claims. Thus it is obvious that the details need not be exactly identical with those shown in the figures and described in the text, but the other solutions are also possible within the spirit of invention. The embodiments are described here in connection with LTCC technology, i.e. in the embodiments of for example FIGS. 1 and 2 the layers are made of greensheets used in LTCC technique. It should however be realized that also other elements than LTCC greensheets can be used to form for example the structure described in the claims etc.

The invention claimed is:

1. A gas analyser comprising a multilayer structure including cavities and volumes, the multilayer structure including laminated and fired single layers on top of each other, the cavities and volumes including pneumatically constrictive openings cut in at least one layer to form pneumatic filters including constrictive cavities and volumes with surfaces of adjoining layers, at least an outer surfaces of the multilayer structure being provided with pneumatic inlet/outlet connections for surface mounted devices, the surface mounted devices including pneumatic or/and electronic components.

2. The gas analyser of claim 1, wherein the constrictive cavities and volumes have openings with short narrow areas that create a throttling effect.

3. The gas analyser of claim 1, wherein the constrictive cavities and volumes are made by dimensioning the cavity/volume to form a cavity/volume with a throttling effect.

4. The gas analyser of claim 1, wherein a throttling effect is obtained with a combination of at least two volumes connected with at least one cavity.

5. The gas analyser of claim 1, wherein the volumes are provided with multiple inlets and/or outlets.

6. The gas analyser of claim 1, wherein the pneumatic components comprise a pressure sensor and the electronic components comprise electronic circuitry amplifying and electronically filtering a signal obtained from the pressure sensor.

7. The gas analyser of claim 1, wherein the multilayer structure further comprises perforations through one or more layers that connect the constrictive cavities and volumes in a layer to surfaces of adjoining layers.

8. The gas analyser of claim 1, wherein the constrictive cavities are arranged to open into a space defined by a housing and at least one outer surface of the multilayer structure.

* * * * *